March 16, 1976 A. GROB Plant Pat. 3,843
KALANCHOE PLANT
Filed Sept. 25, 1974
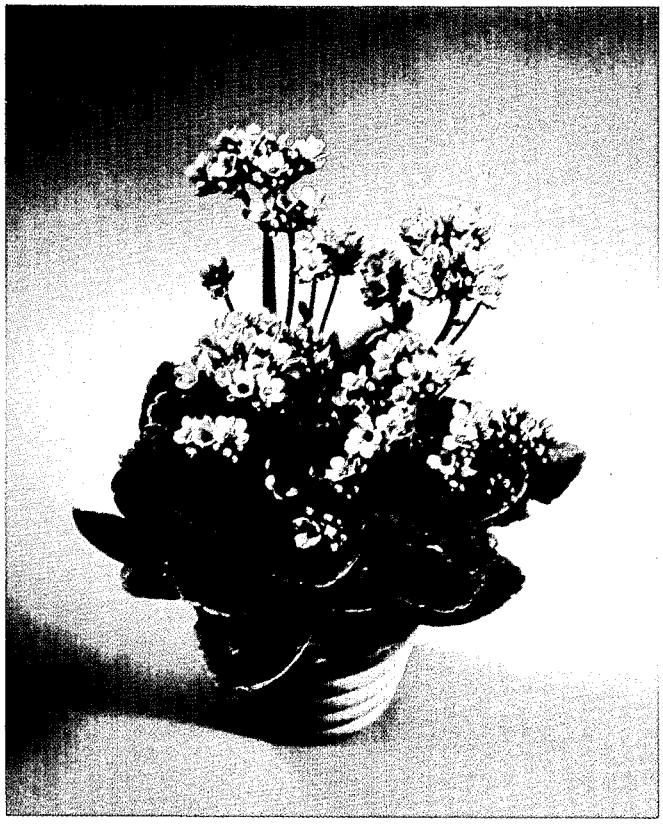

United States Patent

Plant Pat. 3,843
Patented Mar. 16, 1976

1

3,843
KALANCHOE PLANT

Adolf Grob, St. Gallen, Switzerland, assignor to
Mikkelsens Inc., Ashtabula, Ohio Filed Sept. 25, 1974, Ser. No. 509,131
Int. Cl. A01h 5/00
U.S. Cl. Plt.—68 1 Claim The present invention relates to a new and distinct variety of Kalanchoe plant known by the varietal name Solferinopurpur.

The new variety was discovered by me as a selected, cultivated seedling derived from Grobs Improved Amigetti, the unpatented seed parent, and Grobs Segantini, the unpatented pollen parent. The new cultivar was asexually reproduced by vegetative cuttings at St. Gallen, Switzerland, and the unique characteristics of the new cultivar have been transmitted through successive propagations.

The new cultivar is particularly characterized by its dark pink colored flowers, its abundant flowering and compact growth habit, and by its large, flat single flowers which are intense in color. The new cultivar is a semi-dwarf compact type plant and is relatively slow growing, needing two to three weeks additional growth to reach the proper plant size before removal of the apical tip when grown in 5" or 6" pots. Flowering response is fast, wtih flowering taking place eight to ten weeks after flower induction is started.

With respect to the seed parent Grobs Improved Amigetti, perhaps the closest cultivar for comparison purposes, the new cultivar has a more compact growth habit, has a more pure, dark pink flower color, and flowers more regularly.

The following desciption is based on plants of the new cultivar grown initially in St. Gallen, Switzerland and subsequently in Ashtabula, Ohio. Flower color and foliage values are taken from the RHS Colour Chart.

The accompanying color photographic drawing shows a typical blooming plant of the new cultivar, with the color being as true as possible with color illustrations of this type.

Parentage: The new cultivar is a seedling resulting from crossing the seed parent, Grobs Improved Amigetti, an unpatented cultivar, with the pollen parent, Grobs Segantini, also an unpatented Kalanchoe variety.

Propagation: By asexually propagating by cuttings, it has been successfully demonstrated that the new cultivar is stable and produces true to type.

Form: Bush form, semi-dwarf, with numerous branches; compact.

Growth habit: Medium to stumpy and compact: upright and branching due to slow growth, an additional two weeks must be given before pinching and an additional week after pinching before induction of flowering begins.

Rooting: Growth of roots medium relative to semi-dwarf type growth.

2

Blooming habit: Reacts well to short day treatment, flowering period approximately 2–3 months; flowers in 8 to 10 weeks after beginning of flower initiation.

Blooming season: Natural blooming season is January–February, although by short day treatment, flowering of the cultivar is possible year around.

Foliage: Is very plentiful and attractive with purple edges on mature leaves. Foliage is at 45° angle upward, to the stem, leaves opposite.

*Size.*—Small, being approximately 6 cm. in diameter, leaf petiole is very short, approximately 10 to 15 mm. long.

*Shape.*—Oval to orbicular, basically flat.

*Texture.*—Smooth, thick, fleshy, firm, coriaceous.

*Margin.*—Crente, mature leaves have purple edging.

*Color.*—Upperside, nearly yellow green 147A; underside, nearly yellow green 147B—some red infusion when matured.

Disease resistance: No diseases seen to date. Very resistant to mildew when grown with cultivars infected with common powdery mildew.

Flowers:

*Borne.*—On a compound cyme. Flower stems are quite short, often being as close as five or six cm. from the point of origin, average length 9 to 12 cm. long. Because of compact growth characteristic, premature flowering sometimes occurs in lower areas of plants. Flowering response is quite rapid in proper environments.

*Quantity.*—Normal to above normal depending on the amount of growth developed prior to flower induction.

*Flower buds.*—Light red 51A–B covered by four light green sepals before opening. Buds will measure 4–5 mm. just before opening.

*Petals.*—Four petals (occasionally 5–7), separate and distinct, nearly oval measuring 5 mm. wide by 7 mm. long. Total flower diameter approximately 14 mm. to 16 mm. Color Red Purple 57B–C fading to 57–D, reverse side becoming toward Red Purple 67–C.

Reproductive organs:

*Stamens.*—Eight in number, fairly uniform in development. Anthers brown, filament translucent to light green.

*Pollen.*—Yellowish brown.

*Styles/ovaries.* — Four styles, stigmas light green turning pinkish white when receptive, four ovaries each developing multiple seeds.

I claim:

1. A new and distinct cultivar of Kalanchoe characterized particularly by its dark pink colored flowers; abundant flowering, compact growth habit; and large flat single flowers.

No references cited.

ROBERT E. BAGWILL, Primary Examiner